US009082166B2

(12) United States Patent
Yu et al.

(10) Patent No.: US 9,082,166 B2
(45) Date of Patent: Jul. 14, 2015

(54) METHOD AND APPARATUS FOR AUTOMATED PLATELET IDENTIFICATION WITHIN A WHOLE BLOOD SAMPLE FROM MICROSCOPY IMAGES

(71) Applicant: Abbott Point of Care, Inc., Princeton, NJ (US)

(72) Inventors: Changhua Yu, Princeton, NJ (US); Min Xie, Plainsboro, NJ (US); Yiming Wu, Tallahassee, FL (US)

(73) Assignee: Abbott Point of Care, Inc., Princeton, NJ (US)

( * ) Notice: Subject to any disclaimer, the term of this patent is extended or adjusted under 35 U.S.C. 154(b) by 182 days.

(21) Appl. No.: 13/730,095

(22) Filed: Dec. 28, 2012

(65) Prior Publication Data
US 2013/0170730 A1    Jul. 4, 2013

Related U.S. Application Data (60) Provisional application No. 61/581,887, filed on Dec. 30, 2011.

(51) Int. Cl.
*G06K 9/00* (2006.01)
*G06T 7/00* (2006.01)
*G01N 33/86* (2006.01)

(52) U.S. Cl.
CPC .............. *G06T 7/0012* (2013.01); *G01N 33/86* (2013.01); *G06K 9/00147* (2013.01); *G06T 2207/10056* (2013.01); *G06T 2207/30024* (2013.01); *G06T 2207/30242* (2013.01)

(58) Field of Classification Search
CPC ................... G06T 7/0012; G06T 2207/30024; G06T 2007/30242; G06T 2207/10056; G01N 33/86

USPC .......................................... 382/100, 128–134
See application file for complete search history.

(56) References Cited

U.S. PATENT DOCUMENTS

| 4,125,828 A | 11/1978 | Resnick et al. |
| 5,715,334 A * | 2/1998 | Peters ........................... 382/254 |
| 7,850,916 B2 | 12/2010 | Wardlaw |

(Continued)

FOREIGN PATENT DOCUMENTS

FR    2551551    3/1985

OTHER PUBLICATIONS

Vecchione et al. "Enumeration of Previously Frozen Platelets Using the Coulter Counter Phase Microscopy and the Technicon Optical System", Transfusion, vol. 21, No. 5, Jan. 1, 1981, pp. 511-516.

(Continued)

*Primary Examiner* — Shefali Goradia
(74) *Attorney, Agent, or Firm* — O'Shea Getz P.C.

(57) ABSTRACT

A method and apparatus for identifying platelets within a whole blood sample. The method includes the steps of: a) adding at least one colorant to the whole blood sample, which colorant is operable to tag platelets; b) disposing the blood sample into a chamber defined by at least one transparent panel; c) imaging at least a portion of the sample quiescently residing within the chamber to create one or more images; and d) identifying one or more platelets within the sample using an analyzer adapted to identify the platelets based on quantitatively determinable features within the image using a analyzer, which quantitatively determinable features include intensity differences.

20 Claims, 7 Drawing Sheets

(56) References Cited

U.S. PATENT DOCUMENTS

| | | |
|---|---|---|
| 7,929,121 B2 | 4/2011 | Wardlaw et al. |
| 8,009,894 B2 * | 8/2011 | Lindberg et al. .............. 382/141 |
| 2005/0002826 A1 | 1/2005 | Oguni et al. |
| 2006/0258018 A1 * | 11/2006 | Curl et al. .................... 436/180 |
| 2009/0238439 A1 | 9/2009 | Wardlaw et al. |
| 2011/0206557 A1 | 8/2011 | Phan |
| 2012/0219457 A1 | 8/2012 | Verrant |

OTHER PUBLICATIONS

International Search Report for PCT/US2012/072068 dated Apr. 29, 2013.

* cited by examiner

FIG. 6
(WBCs platelets)

FIG. 7
(blood/glueline)

*FIG. 8*
(Sample/air interface)

*FIG. 9*
(Chamber entry area)

FIG. 15

METHOD AND APPARATUS FOR AUTOMATED PLATELET IDENTIFICATION WITHIN A WHOLE BLOOD SAMPLE FROM MICROSCOPY IMAGES

The present application is entitled to the benefit of and incorporates by reference essential subject matter disclosed in the U.S. Provisional Patent Application Ser. No. 61/581,887, filed Dec. 30, 2011.

BACKGROUND OF THE INVENTION

1. Technical Field

The present invention relates to methods and apparatus for performing analyses on whole blood samples from microscopy images in general, and to automated version of the same involving platelets in particular.

2. Background Information

Medical diagnostics often include analyses of a whole blood sample from a patient. One of the more popular diagnostics is a complete blood count (referred to as a "CBC"), which is a suite of tests that includes a "platelet count" (i.e., a thrombocyte count). The platelet count is actually a concentration determination; i.e., number of platelets per volume. In an adult, a normal platelet count is typically about 150,000 to 450,000 platelets per microliter of blood. An abnormal platelet count can be an indicator of a health problem; e.g., infection, disease, etc. If platelet levels fall below 20,000 per microliter, spontaneous bleeding may occur and is considered a life-threatening risk.

Historically, platelet counts have been performed either by smearing a small amount of undiluted blood on a slide or by flow cytometry. In the case of the smear, the sample is applied to a slide and the platelets and other constituents residing within the smear are counted. The platelet count (i.e., platelets per volume within the sample) is estimated based on the relative constituents within the sample.

To perform a platelet count via an electrical impedance or optical flow cytometer, the blood sample must be diluted and then sent through a small vessel wherein electrical impedance or optical sensors can evaluate constituent cells within the sample as they pass serially through the vessel. The accuracy of these devices can suffer, depending upon the constituents present within the sample. In an impedance counter, for example, red blood cell fragments can be construed and counted as platelets, and giant platelets can be construed and counted as red blood cells (RBCs). In both instances, the accuracy of the automated platelet count suffers. In addition, the dilution of the sample must be precise or the accuracy is negatively affected, and the diluted sample must be properly disposed of post-analysis. The internal plumbing required to handle the diluted sample often requires maintenance and at best contributes considerably to the complexity and cost of the device.

What is needed is an apparatus and method for performing automated analyses on a whole blood sample, including a platelet count, which can overcome the limitations of the prior art, including the time required to perform the analysis, the operator skill level required to perform the analysis, and one that can provide greater versatility than known prior art methods and apparatus.

SUMMARY OF THE INVENTION

According to an aspect of the present invention, a method for identifying platelets within a whole blood sample is provided. The method includes the steps of: a) adding at least one colorant to the whole blood sample, which colorant is operable to tag platelets; b) disposing the blood sample into a chamber defined by at least one transparent panel; c) imaging at least a portion of the sample quiescently residing within the chamber to create one or more images; and d) identifying one or more platelets within the sample using an analyzer adapted to identify the platelets based on quantitatively determinable features within the image using a analyzer, which quantitatively determinable features include intensity differences.

According to another aspect of the present invention, an apparatus for identifying platelets within a whole blood sample is provided. The apparatus includes an analysis cartridge and an analysis device. The analysis cartridge has an analysis chamber with a pair of planar members, at least one of which is transparent. At least one colorant is added to the whole blood sample (e.g., within the cartridge), which colorant is operable to tag platelets. The chamber is operable to hold the sample quiescently between the planar members. The analysis device is operable to image at least a portion of the sample quiescently residing within the chamber. The analysis device is adapted to identify the platelets based on quantitatively determinable features within the image, which quantitatively determinable features include intensity differences.

According to an embodiment of the present invention, intensity differences in local regions within the image are determined.

According to an embodiment of the present invention, an image intensity of plasma is accounted for.

According to an embodiment of the present invention, platelet candidates are evaluated using a directional contrast of an intensity difference.

According to an aspect of the present invention, the image is evaluated to determine a presence of one or more platelet clusters within the sample.

According to an aspect of the present invention, platelet candidates within the image are identified and analyzed using a rule based classifier that uses a plurality of quantitative features.

The above described aspects of the present invention and embodiments may be used individually or in combination with one another, and the present invention is not limited to any particular configuration. These and other aspects, embodiments, features, and advantages of the present invention will become apparent in light of the detailed description of the invention provided below, and as illustrated in the accompanying drawings.

DETAILED DESCRIPTION OF THE INVENTION

Figure 1:
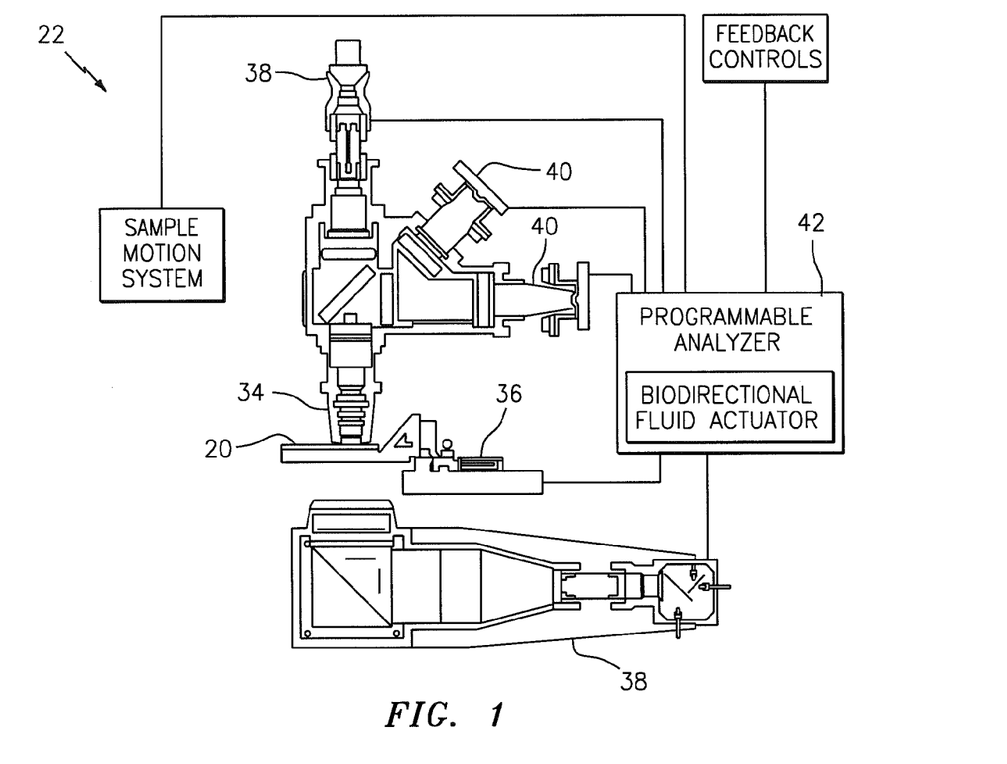
FIG. 1 is a diagrammatic view of an analysis device operable to perform a platelet analysis according to the present invention.
Figure 2:
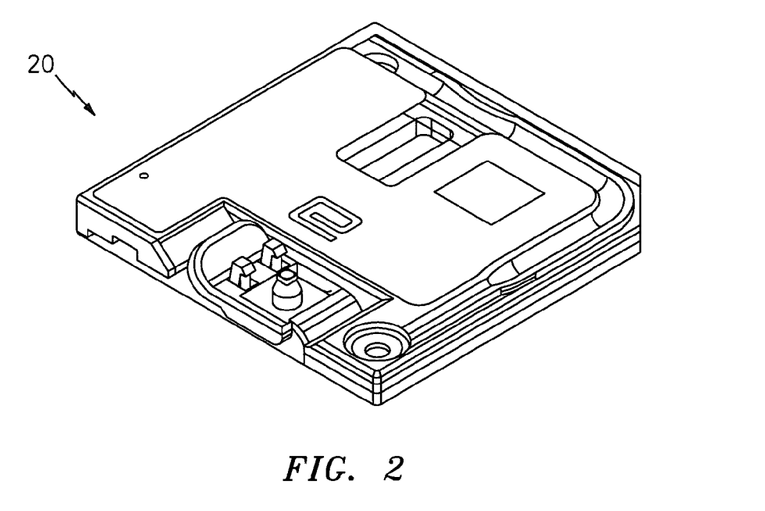
FIG. 2 is a perspective view of an analysis cartridge having an analysis chamber that can be used with the present invention.

Referring to FIGS. 1 and 2, aspects of the present invention include a method and an apparatus for identifying and enumerating platelets within a blood sample quiescently residing within an analysis chamber. The analysis chamber is typically included within a cartridge 20 that is configured for use with an automated analysis device 22, which device has imaging hardware and a programmable analyzer adapted to acquire and analyze images of the sample and thereby identify and enumerate platelets within the sample.

Figure 3:
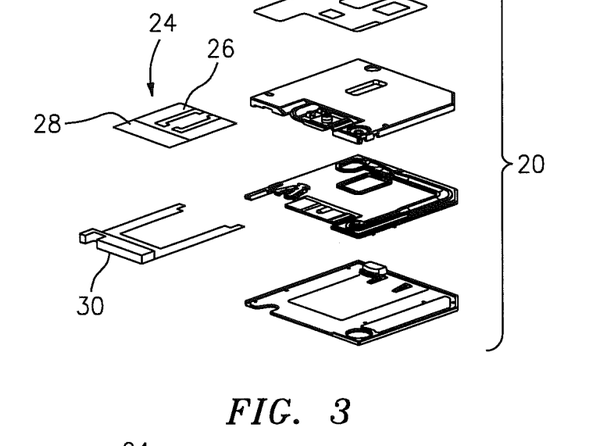
FIG. 3 is an exploded view of the cartridge shown in FIG. 2
Figure 4:
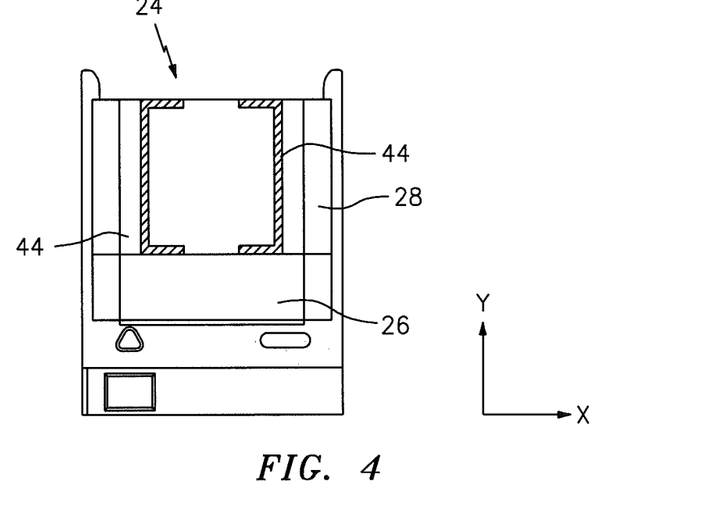
FIG. 4 is a top planar view of a tray holding an analysis chamber.
Figure 5:
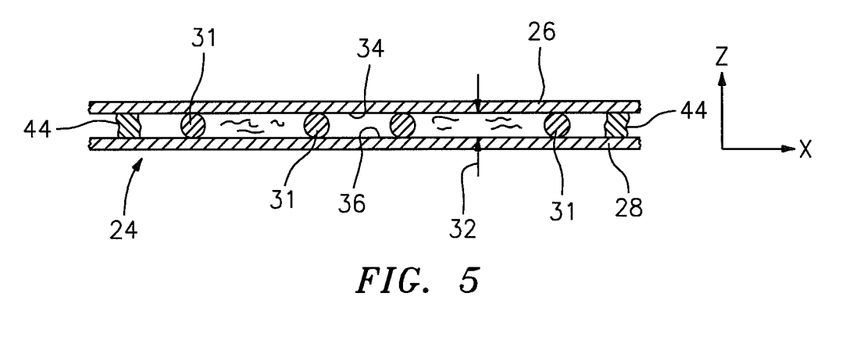
FIG. 5 is a diagrammatic sectional view of an analysis chamber.

Referring to FIGS. 2-5, the present invention is not limited to use with any particular analysis chamber embodiment. Examples of acceptable analysis chambers (and accompanying cartridges) are described in U.S. Pat. No. 7,850,916, and U.S. patent application Ser. Nos. 12/971,860; 13/341,618; and 13/594,439, each of which are incorporated herein by reference in its entirety. For purposes of this disclosure, the invention will be described as using the cartridge and analysis chamber described in U.S. patent application Ser. No. 13/594,439. The analysis chamber 24 disclosed in the '439 application includes an upper planar member 26 and a base planar member 28 attached to a tray 30 that is removably mounted within the cartridge 20. In some embodiments, a plurality of separator beads 31 (e.g., uniformly sized beads) are disposed between the upper and base planar members 26, 28, typically in contact with the opposing surfaces of the planar members. FIG. 2 shows the cartridge 20 in assembled form. FIG. 3 shows an exploded view of the cartridge 20, including the analysis chamber 24 and the tray 30. FIG. 4 is a top view of the analysis chamber 24 mounted on the tray 30, and shows an X-Y plane view of the chamber 24. FIG. 5 is a diagrammatic cross-section of the chamber 24, illustrating a Z-X plane view of the chamber 24. The height 32 of the chamber 24 extends along the Z-axis, extending between the opposing interior surfaces 34, 36 of the planar members. For whole blood sample analyses, the height 32 of the chamber 24 is preferably about four microns (4 µm), but the chamber 24 is not limited to that height.

Referring to FIG. 1, an analysis device 22 operable to be used with the above described chamber 24 typically includes an objective lens 34, a cartridge positioner 36, one or more sample illuminators 38, one or more image dissectors 40, and a programmable analyzer 42. One or both of the objective lens 34 and cartridge positioner 36 are movable toward and away from each other to change a relative focal position of the device relative to the chamber 24 and the sample disposed therein.

The sample illuminator 38 illuminates the sample using light along predetermined wavelengths. For example, the sample illuminator 38 can include an epi-fluorescence light source and a transmission light source. As will be explained below, a colorant such as Acridine Orange (also referred to as "Basic Orange 15" or "ACO") emit light at particular wavelengths when mixed with whole blood and subjected to an excitation wavelength from the epi-fluorescent light source, which source typically produces light within the range of about 450-490 nm. An excitation wavelength at about 470 nm is particularly useful. The transmission light source is operable to produce light at wavelengths associated with red and green light, for example. The red light is typically produced in the range of about 600-700 nm, with red light at about 660 nm preferred. The green light is typically produced in the range of about 515-570 nm, with green light at about 540 nm preferred. Light transmitted through the sample, or fluoresced from the sample, is captured using the image dissector 40, and a signal representative of the captured light is sent to the programmable analyzer 42, where it is processed into an image. The image is produced in a manner that permits the light transmittance or fluorescence intensity captured within the image to be determined on a per unit basis; e.g., "per unit basis" being an incremental unit of which the image of the sample can be dissected, such as a pixel.

An example of an acceptable image dissector 40 is a charge couple device (CCD) type image sensor that converts light passing through (or from) the sample into an electronic data format image. Complimentary metal oxide semiconductors ("CMOS") type image sensors are another example of an image sensor that can be used. The signals from the image dissector 40 provide information for each pixel of the image, which information includes, or can be derived to include, intensity, wavelength, and optical density. Intensity values are assigned an arbitrary scale of, for example, 0 units to 4095 units ("IVUs"). Optical density ("OD") is a measure of the amount of light absorbed relative to the amount of light transmitted through a medium; e.g., the higher the "OD" value, the greater the amount of light absorbed during transmission. OD can be quantitatively described in optical density units ("ODU") or fractions thereof; e.g., a MilliODU is a $1/1000^{th}$ of an ODU. One "OD" unit decreases light intensity by 90%. "ODU" or "MilliODU" as a quantitative value can be used for images acquired or derived by transmission light. The information from the image dissector 40 may be separated into multiple channels. For example, the information from the image dissector 40 may be separated into three channels. The present invention is not limited to a three channel embodiment, however. A first of the three channels may be directed toward information relating to light emitted from the sample at a first wavelength (e.g., 540 nm, which appears green). A second channel may be directed toward information relating to light emitted from the sample at a second wavelength (e.g., 660 nm, which appears red). A third channel may be directed toward information relating to light passing through the sample at a third wavelength (e.g., 413 nm, which is used to determine blue optical density—"OD"). The present invention is not limited to these particular wavelengths or number of channels.

The programmable analyzer 42 includes a central processing unit (CPU) and is in communication with the cartridge positioner 36, the sample illuminator 38, and the image dissector 40. The programmable analyzer 42 is adapted (e.g., programmed) to send and receive signals from one or more of the cartridge positioner 36, the sample illuminator 38, and an image dissector 40. For example, the analyzer 42 is adapted to: 1) send and receive signals from the cartridge positioner 36 to position the cartridge and chamber 24 relative to one or more of the optics, illuminator 38, and image dissector 40; 2) send signals to the sample illuminator 38 to produce light at defined wavelengths (or alternatively at multiple wavelengths); and 3) send and receive signals from the image dissector 40 to capture light for defined periods of time. It should be noted that the functionality of the programmable analyzer 42 may be implemented using hardware, software, firmware, or a combination thereof. A person skilled in the art would be able to program the processing unit to perform the functionality described herein without undue experimentation.

The programmable analyzer 42 is further adapted to process the signals received from the image dissector 40 according to algorithms that identify platelets within the sample image, and to distinguish platelets from image characteristics that are similar to platelets, but are not platelets, and from background characteristics that obscure platelets.

The analysis device 22 is adapted to image a substantially undiluted whole blood sample disposed within the analysis chamber 24. The sample is mixed with an amount of a fluorescent dye (or other colorant) that is operable to stain the platelets contained within the sample. The addition and mixing of the dye with the sample could occur at any time prior to the imaging of the sample; e.g., mixed in the channels of the cartridge prior to passing into the chamber 24 via capillary flow. The dye permeates through and stains the respective platelets. The dye, upon excitation, produces fluorescent light emission at particular wavelengths associated with particular colors. The specific color(s) and intensity of the light emitted by the dye within the platelet are typically a function of a number of factors, including: the concentration of the dye within the platelet, and the pH of the platelet. As will be described below, the fluorescent light emission produces localized peak emission regions that represent the platelet from which they are being emitted.

An example of an acceptable colorant that can be used when performing a platelet count in a whole blood sample is Acridine Orange ("ACO"). ACO is a fluorescent dye that, when mixed with a whole blood sample, stains the platelets (and WBCs 50 and reticulocytes) within the sample. The present invention is not limited to using ACO, and other dyes (e.g., Astrazon Orange) may be used in place of ACO or in combination with ACO. Using ACO as an example, if the sample is subjected to an excitation light at or about a wavelength of 470 nm, the ACO within the platelet will emit light at about 540 nm (which appears green) and light at about 660 nm (which appears red).

To perform the platelet count, the analyzer 42 is adapted (e.g., programmed with an algorithm) to direct the sample illuminator 38 to illuminate the sample quiescently residing within the sample with excitation light (e.g., light at about 470 nm) and transmission light (e.g., light at about 413 nm and at about 660 nm). Upon encountering the excitation light, the fluorescent dye within each platelet emits green light at about 540 nm and red light at about 660 nm. The fluorescent light emitted from the sample and the transmission light passing through the sample is captured using the image dissector 40, and a signal representative of the captured light is sent to the programmable analyzer 42, where it is processed into an image. The image is produced in a manner that permits the fluorescence and transmission intensity captured within the image to be determined on a per unit basis.

The programmable analyzer 42 is adapted to collect the image data signals from the image dissector 40 and process those image data signals to facilitate the identification of platelets shown within the image. The programmable analyzer 42 is also adapted to determine the volume of the sample quiescently residing within the analysis chamber 24. For example, the algorithm is adapted to identify perimeters of the sample within the chamber 24 such as glue line 44/sample 46 interfaces (e.g., see FIG. 7), which glue lines 44 form lateral boundaries of the chamber 24, and sample 46/air 48 interfaces 49 (e.g., see FIG. 8) that exist typically at the edges of the sample 46 that do not encounter a glue line 44. The height 32 of the chamber 24 is known or determinable. Once the area of the chamber 24 occupied by the sample 46 is determined (e.g., each pixel of the image has an associated chamber area), the volume of the sample can be determined using the sample area and the height associated with the chamber 24.

Figure 6:
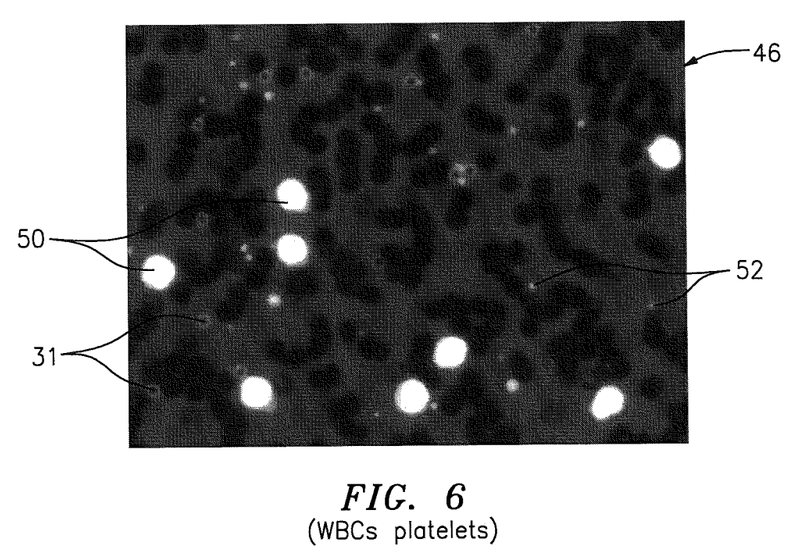
FIG. 6 is an image showing platelets and white blood cells within a sample under fluorescent imaging.

In some embodiments the image data signals are initially processed with a smoothing algorithm that filters the signals to make the background portions of the image more uniform. An example of an acceptable smoothing algorithm is one that applies a morphology filter (e.g., an image opening filter) to the image data. The filter is operable to alleviate some background variations and can be used to remove large bright objects from the image such as white blood cells 50 ("WBCs"). WBCs 50 can appear as intensity peaks due to material contained within the WBCs 50 (e.g., RNA, DNA) that is highlighted by the colorant used to highlight the platelets. FIG. 6 illustrates platelets 52 and WBCs 50 within an image. WBCs 50 can be distinguished from platelets 52, however, based on their large light intensity relative to platelets 52. Eliminating the WBCs 50 from the image (e.g., by a segmentation process) facilitates the identification of the platelets 52.

The image data is also analyzed to identify local intensity peaks. This local peak identification process can be performed before or after the "smoothing" process, but performing the smoothing step first eliminates some potential sources of error prior to the local peak intensity determination. This smoothing step is not required, however. The identification of the local intensity peaks at one or more defined wavelengths can be performed using a variety of different techniques. As will be described below, image intensity can vary substantially throughout the sample, which variations can be attributable to factors such as plasma intensity variation, glue line proximity, WBC concentration, RBC concentration, etc. The accuracy of the platelet identification is enhanced by quantitatively evaluating intensity differences (i.e., peaks) on a local basis. The term "local" as used herein refers to defined small areas within the sample quiescently residing within the chamber 24, which areas can be defined in terms of a predetermined pixel region; e.g., a 5×5 square of pixels. A 5×5 pixel square is useful when evaluating platelets 52 because a typical platelet 31 of about 2-3 μm size fits within the 5×5 pixel square at the resolution used for the imaging. The present invention is not limited to "local regions" of this particular size, however. In each of these local regions, a maximum sample image intensity value is determined. For example, the sample can be subjected to a fluorescent excitation light, and a sample image acquired, which image includes emitted light intensity; e.g., emitted light intensities within the green fluorescent channel. Once the image intensity peaks are determined in the respective local regions, a global threshold can be applied to eliminate those intensity peaks (e.g., maximums) below the global threshold. This identification process establishes all of the portions within the image that can potentially represent a platelet 31, which portions are each referred to hereinafter as a "platelet candidate". Once all of the potential platelet candidates are identified, then the image data is further analyzed to eliminate those candidates that are not platelets 52, and to identify platelet clumps that may be present within the image.

Figure 7:
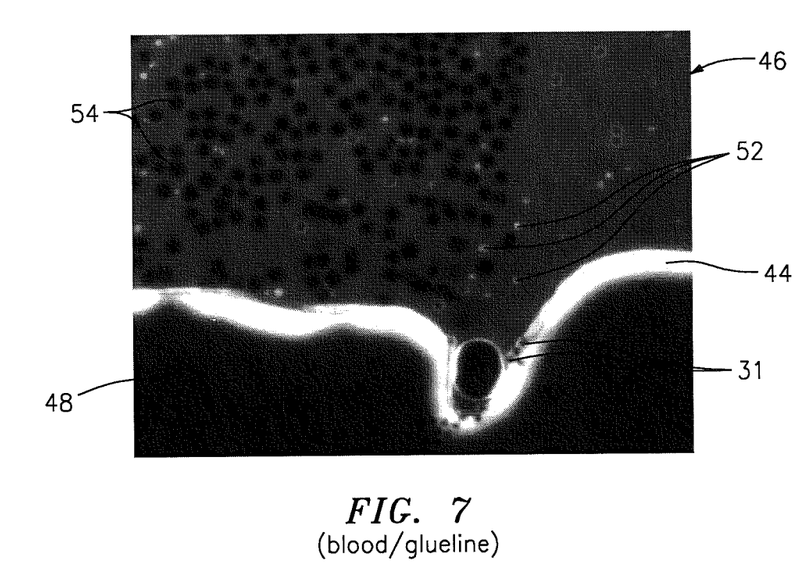
FIG. 7 is an image showing a glue line/sample interface.
Figure 8:
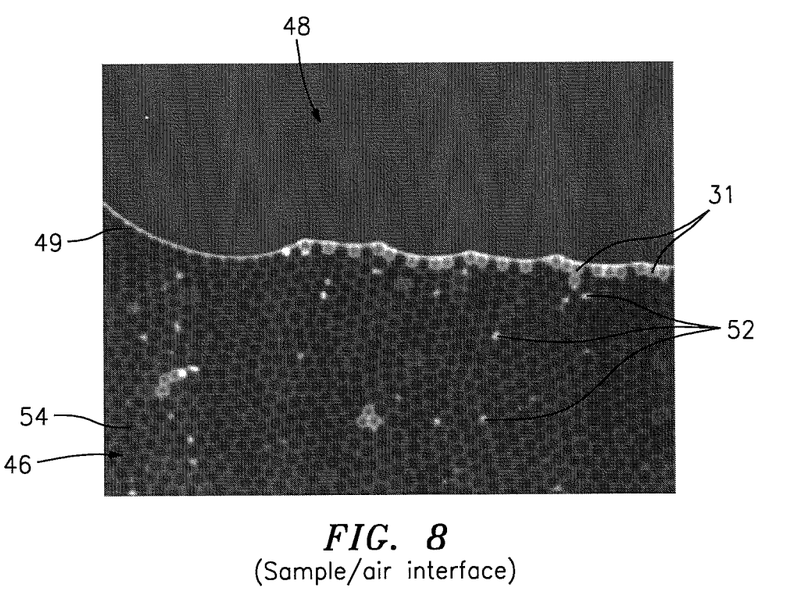
FIG. 8 is an image showing a sample/air interface.

The image intensity of the sample image portions that are contiguous with the analysis chamber glue lines 44 and the sample/air interface(s) 49 can be contaminated by light intensity effects caused by the glue lines 44 and the sample/air interface(s) 49. For example, as can be seen in FIG. 7, when the sample is illuminated the glue lines 44 appear bright, having high image intensity. The high image intensity of the glue lines 44 causes the contiguous areas to have greater intensity than they would otherwise, thereby increasing the possibility of mistaken platelet identification, or the possibility that platelets 52 will be missed because of the overall intensity. The same effect occurs to some degree at the sample/air interface 49 as can be seen in FIG. 8. A technique that can be algorithmically implemented by the analyzer 42 to account for the intensity contamination in the contiguous image portions (i.e., anomaly areas) is to remove those contiguous image portions from consideration during the platelet count; e.g., by masking, etc. The determination of how much sample image is removed may be made, for example, by evaluating relevant historical data. For example, removal of about 100 pixel lines of the sample image contiguous with a glue line is typically adequate to eliminate intensity contamination attributable to that glue line 44. Similarly, removal of about 80 pixel lines of the sample image contiguous with a sample/air interface 49 is typically adequate to eliminate intensity contamination attributable to that interface. To account for platelets 52 present in the removed sample image portions, the number of platelets in that area can be estimated based on relative numbers of platelets determined in regions of the sample image local to the removed area.

Figure 9:
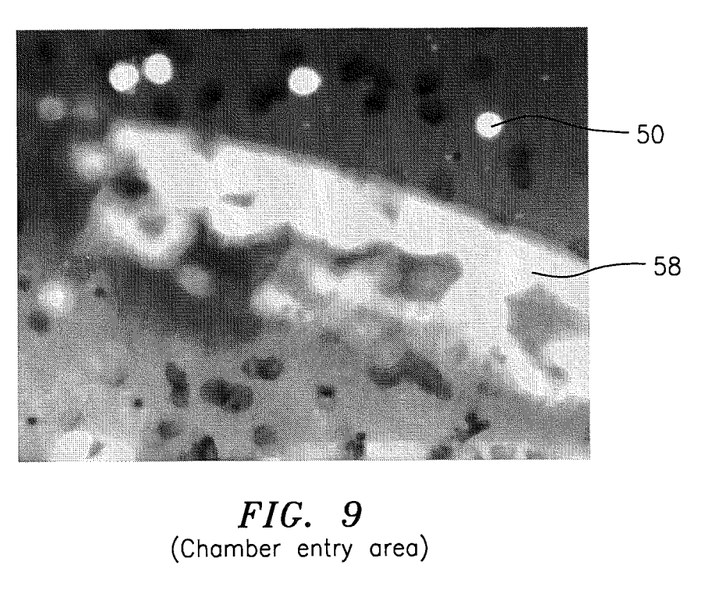
FIG. 9 is an image of a sample entry region of a chamber.

In some embodiments, the algorithm utilized within the processor 42 can be further adapted to recognize other areas where platelet recognition is problematic. For example, in some instances a region of an analysis chamber 24 may have discrepancies that will inhibit an accurate volume determination. In such an instance, the ability to do an accurate platelet count (which is a function of volume) in that area may be compromised. FIG. 9, for example, shows a chamber entry region that has image anomalies 58 due to excessive sample in the area. To account for such anomalies, the number of platelets 52 in the area can be estimated based on platelet counts in areas of the sample local to the problematic area.

Another technique for facilitating the identification of the platelets 52 that can be algorithmically implemented by the analyzer 42 is a removal of background existing within the initially acquired image. For example, a filter can be applied to the image data signals that removes variations in intensity (e.g., green light intensity) below a predetermined global threshold. Local intensity maximums below the global threshold that might otherwise be identified as platelets 52 can be eliminated, thereby eliminating the possibility that those intensity peaks are incorrectly identified as platelets 52. Segmentation techniques, for example, can be used as a mechanism for removing the background. The present invention is not limited to any particular segmentation technique, and a specific technique can be chosen in view of the application at hand. The present invention is also not limited to using a segmentation technique to remove background, and can use other techniques that select (i.e., "pick") pixels or otherwise distinguish pixels having particular attributes.

Another technique for facilitating the identification of the platelets 52 that can be algorithmically implemented by the analyzer 42 involves accounting for (e.g., estimating) the image intensity of plasma within local areas of the sample. Plasma typically appears brighter (i.e., higher image intensity) than RBCs but not as bright as platelets 52. At least some of the fluorescent dye added to the sample can reside within the plasma, and as a result illuminating the sample with excitation light creates some level of emitted light intensity within the plasma. The distribution of dye within the plasma may not, however, be uniform within the entire sample. Consequently, the image intensity of plasma can vary significantly within the sample disposed within the analysis chamber 24. For example, imaging data indicates that the image intensity of plasma within a first area of the sample can vary as much as 30-40% from the image intensity of plasma in a second area of the sample. The lack of uniformity within the plasma intensity makes it difficult to uniformly account for plasma intensity without negatively affecting the platelet identification process. The non-uniformity of plasma intensity is particularly problematic in regions within the sample where large numbers of RBCs 54 reside. If the plasma intensity is not accounted for, small areas of plasma visible within RBC regions can appear as local intensity peaks which could then be mistakenly identified as platelets 52. To address this issue, the algorithm can be adapted to apply a RBC mask in the RBC regions to segment out the RBCs 54 (or otherwise remove them from the image), leaving the remaining plasma areas. For example, RBCs 54 have no expression in the red channel of image signal data. An image formed using a red channel mask, therefore, will only show the intensity of the plasma and whatever platelets 52 are within that RBC region. The platelets 52 can then be quantitatively distinguished from the local plasma by virtue of the difference in intensity (e.g., those pixels that are about 20% greater than the surrounding pixels) between the two sample constituents. In those RBC regions that do not have sufficient plasma areas to permit this type of comparative analysis, an alternative technique can be used based on the image intensity of the RBCs 54 themselves. For example, the estimated plasma image intensity in those regions can be based on the following estimation: (RBC average image intensity)+3*(RBC image intensity standard deviation)=estimated plasma intensity. The present method is not limited to this particular alternative technique.

Figure 10:
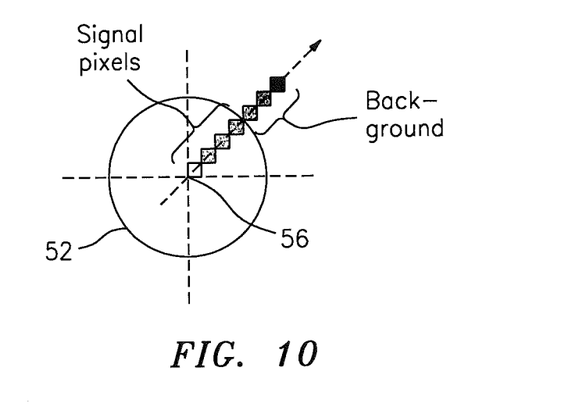
FIG. 10 is a diagrammatic illustration of intensity directional contrast within a platelet.

After one or more of the above described techniques are applied to the platelet candidates and non-platelet candidates (to the extent they are identified) are removed from consideration, the remaining candidates can be further analyzed by evaluating the characteristics of each individual candidate. A first technique that can be algorithmically implemented by the analyzer 42 involves evaluating the directional contrast of the candidate's intensity peak within a given area. The area can be defined in terms of pixels surrounding the intensity peak. For example, using a resolution that is useful for a whole blood analysis (e.g., 0.5 µm/pixel), the area potentially representing the platelet candidate can be defined as up to about three or four (3 or 4) pixels outwardly from the intensity peak, and the area outside of the four (4) pixels defined as being outside the platelet candidate. The present invention is not limited to these area definitions, which can be selected to suit the application at hand. Platelets 52 have a directional intensity contrast within the defined area, wherein the intensity decreases outwardly from the center of the area (i.e., outwardly from the intensity peak, diagrammatically shown in FIG. 10) in a direction toward the perimeter of the area. For example, the intensity of the peak is at a maximum in the center and decreases along a slope extending outwardly toward the area perimeter. In terms of the image, which is step-wise segmented by the pixels forming the image, each pixel has a decrease in intensity traveling in the direction toward the area perimeter. This incremental decrease in intensity exists in a plurality of directions out from the maximum intensity value at the center of the area, but not necessarily in all directions. The circumferential uniformity of the directional intensity contrast can be evaluated by quantitatively evaluating the image intensity of pixels every "Y" degrees of rotation (e.g., every 30 degrees) around the intensity peak of the candidate. The rate of the intensity decrease per pixel can also vary to suit the application at hand. In addition, a first intensity decrease percentage can be used in a first region of the sample, and a second higher percentage in other regions of the sample where platelet identification is more difficult; e.g., use a higher intensity decrease percentage in regions of higher plasma intensity, or in RBC regions. FIG. 10 diagrammatically depicts an intensity peak of a platelet candidate, illustrating an incremental decrease in intensity from the center of the area outwardly in a single direction toward the perimeter of the area.

Figure 11A:
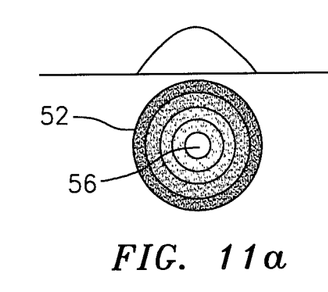
FIGS. 11a-11c are diagrammatic illustrations of Gaussian distributions of image intensity within a platelet candidate.
Figure 11B:
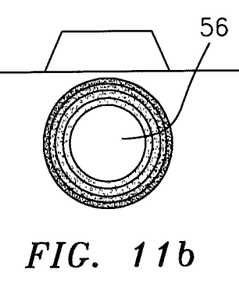
Figure 11C:
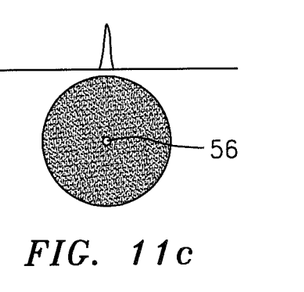

Another technique for algorithmically evaluating the characteristics of an individual candidate involves quantitatively determining a Gaussian distribution of the incremental decrease in intensity surrounding the candidate's intensity peak in a given area (which area is defined above relative to directional contrast). FIGS. 11a-11c diagrammatically illustrate three different Gaussian distributions of intensity surrounding an intensity peak. In FIG. 11a, a sharply defined intensity peak is located in the center of the area, and the intensity distribution decreases uniformly traveling away from the center peak; e.g., pixel to pixel decrease in intensity of about 4%. This intensity distribution is very typical of platelet images and platelet candidates having this distribution are accepted as platelet images. In FIG. 11b, the distribution illustrates an intensity peak within the area center, surrounded by a region of nearly the same intensity (e.g., less than 3% variation in intensity amongst the central pixels), which region in turn is surrounded by a region of relatively large intensity decrease in the outward direction. This intensity distribution (which appears as having a large intensity peak area) is less typical of platelet images and may be a function of the image being over exposed. Depending upon the circumstances of the image, platelet candidates having this type of Gaussian distribution may be accepted as a platelet; e.g., accepted when they favorably compare to local plasma intensity values, etc. In FIG. 11c, the distribution illustrates a relatively sharp intensity peak within the center of the area, surrounded by a sharp decrease in intensity in the outward direction. This intensity distribution is not indicative of a platelet, and these platelet candidates are not accepted as platelets 52. One or both of the Gaussian distribution and directional contrast analyses can be performed on a platelet candidate.

Within a sample of substantially undiluted whole blood, platelets 52 can aggregate into clusters that show up in the image as a mass having multiple intensity peaks. If a cluster is considered to be only a single platelet, the number of platelets 52 identified will be less than are actually present in the cluster. To avoid this type of error, the analyzer 42 can be algorithmically adapted to identify platelet clusters and distinguish them from single platelets 52. One method for identifying and distinguishing the clusters involves the above-described Gaussian distribution analysis. This technique utilizes the outer region of the area defined as a platelet candidate within the Gaussian distribution analysis (e.g., the area within a radius of "x" pixels). To identify a cluster, the image intensity of the pixels at the perimeter are compared to the local plasma intensity. If a number of the candidate perimeter pixels (e.g., 50%) each have an image intensity that is a predetermined percentage greater than the local plasma image intensity, then the candidate is deemed to be a cluster. This is an example of a method for identifying a cluster and the present invention is not limited to this particular example.

Once a cluster is identified, the number of platelets 52 within the cluster can be determined using a variety of techniques. For example, the algorithm can be adapted to determine a threshold image intensity value ($T_h$) for each peak in the cluster. The threshold image intensity value ($T_h$) is determined based on the image intensity value of that particular peak, and a local plasma intensity value. The threshold value ($T_h$) is less than the respective peak intensity value, but is greater than the local background intensity values. To determine the number of platelets 52 within a given cluster, a "grow" technique is applied by the algorithm to the identified cluster. Under the grow technique, the image units (e.g., pixels) that are contiguous with the peak intensity image units, and which have an intensity value equal to or greater than the threshold intensity value ($T_h$), are identified as part of the cluster. The process then applies the same threshold evaluation to the pixels contiguous with the pixels last identified as part of the cluster. The process is repeated until no additional contiguous pixels at an intensity level greater than the threshold level ($T_h$) are found.

Once the cluster is "grown", the area associated with each grown platelet (i.e., each body expanded outwardly from an image intensity peak as described above) within the cluster is determined and an average ($PLT_{avg\ grown\ area}$) area value of those expanded regions is determined. That average area value ($PLT_{avg\ grown\ area}$) is then compared to a known average normal platelet area ($PLT_{avg\ normal\ area}$). If the average grown area ($PLT_{avg\ grown\ area}$) is greater than a multiplier times the average human platelet area (e.g., $\alpha * PLT_{avg\ normal\ area}$, where $\alpha$ may equal 1.x) then the number of platelets 52 within the cluster is defined by the total area of the cluster ($A_{cluster}$) divided by the average human platelet area (e.g., $A_{cluster}/PLT_{avg\ normal\ area}$). If the average grown area ($PLT_{avg\ grown\ area}$) is less than the aforesaid multiplier times the average human platelet area, then the number of platelets 52 within the cluster is defined by the total area of the cluster divided by the average grown platelet area (e.g., $A_{cluster}/PLT_{avg\ grown\ area}$).

Figure 12:
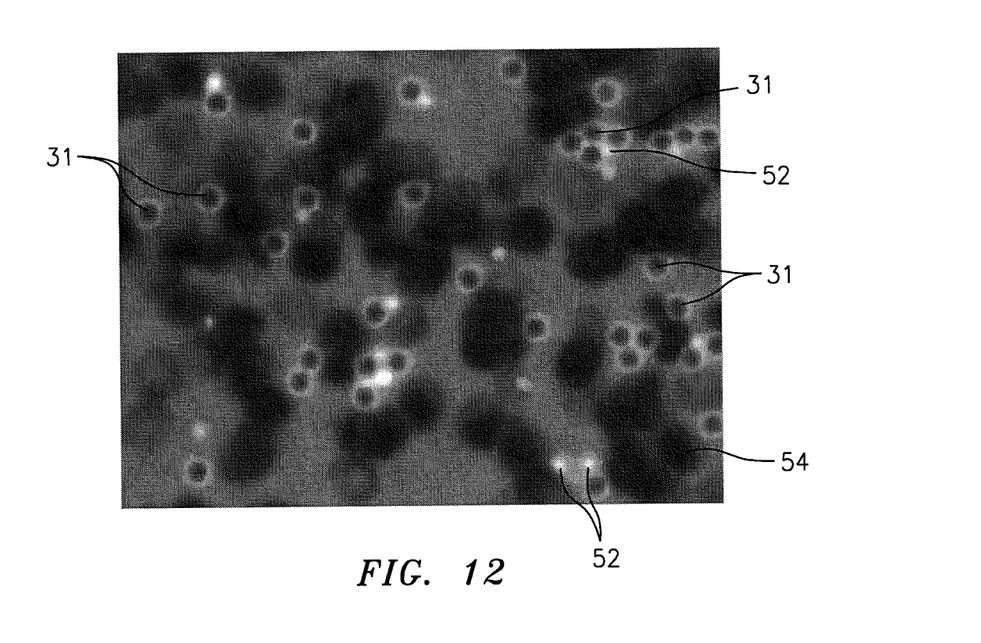
FIG. 12 is an image showing a bead within a sample under fluorescent imaging.

For those platelet analyses that utilize an analysis chamber 24 having beads 31 disposed within the chamber 24 (e.g., a chamber such as that disclosed in the '114 application), the beads 31 may appear in the image as having a bright ring around their perimeter; i.e., a ring of high intensity within the image. The image shown in FIG. 12 includes a plurality of beads 31, each with a ring of high image intensity around its perimeter bead 31.

To avoid possible platelet identification error associated with the beads 31 (e.g., within the bright ring, or in close proximity ring, or inside of the ring), the analyzer 42 can be adapted to evaluate the intensity peaks associated with a bead 31 using a rule based classifier based on a plurality of features. The present invention is not limited, however, to using the classifier solely for the purpose of analyzing bead contiguous regions for platelets 52.

As an initial step, beads 31 are identified within the image sample. For example, beads 31 can be identified within the sample image created to determine the sample volume, in which image they appear as a dark spot; e.g., in some instances the identified beads may be masked to more clearly appear as a dark spot to facilitate the analysis. The invention is not limited to this technique for identifying beads 31, however.

Once a bead 31 is identified, each image intensity peak within the bead area is identified and is considered to be a platelet candidate. To further evaluate a platelet candidate, that candidate may then be subjected to a "grow" technique as is described above to determine whether the candidate is a platelet candidate or possibly a platelet cluster.

For each intensity peak (e.g., located proximate a bead 31) that is identified as a platelet candidate, that candidate may then be further evaluated using the rule based classifier.

Within the steps of the rule based classifier, each platelet candidate is analyzed using at least some of a plurality of quantitative features including: Area, Normalized Peak Intensity Value, Normalized Average Intensity Value, Normalized Estimated Plasma Intensity, Roundness, Extent, Solidity, Eccentricity, Major Axis Length, and Minor Axis Length. These quantitative features are examples of characteristics that can be used within the rule based classifier, but the present invention is not limited to these specific features. In addition, the present invention is not limited to using any particular number or combination of these features; e.g., in some instances the rule based classifier may use as few as one feature or as many as all the features during the classifying process.

For example, to evaluate a particular platelet candidate, the classifier may first consider the candidate Area. A quantitative value for the candidate Area can be assigned based on the number of pixels that the candidate platelet occupies within the image.

The rule based classifier is also adapted to consider a quantitative value representative of a Normalized Peak Intensity Value of the platelet candidate. For example, as indicated above, image intensity values may be assigned an arbitrary scale of, for example, 0 units to 4095 units ("IVUs"). In this feature, the peak image intensity value may be normalized by dividing the determined value by 4095. As indicated above, the intensity scale of 0-4095 is an arbitrary scale and the present invention is not limited to this particular scale.

The rule based classifier is also adapted to consider a quantitative value representative of a Normalized Average Intensity Value of the platelet candidate. In this feature, the image intensity values of the pixels within the platelet candidate are averaged and normalized by dividing the determined value by 4095. Here again, the intensity scale of 0-4095 is an arbitrary scale and the present invention is not limited to this particular scale.

The rule based classifier is also adapted to consider a quantitative value representative of a Normalized Estimated Plasma Intensity of plasma local to the platelet candidate. In this feature, in a manner the same as or similar to that described above, local plasma regions are identified and a representative image intensity value of those plasma regions is determined; e.g., an average intensity value for the local plasma regions is determined. The representative image intensity value for the local plasma regions is then normalized in a manner such as that described above; e.g., the value divided by 4095.

The rule based classifier is also adapted to consider a quantitative value representative of the Roundness of a platelet candidate. One technique for determining the Roundness of a platelet candidate involves utilizing the following equation:

$$\text{Roundness} = \frac{\text{Perimeter}^2}{4\pi \cdot \text{Area}}$$

where the term Perimeter is defined as the distance around the perimeter of the platelet candidate, and the term Area is the area of the platelet candidate.

Figure 13:
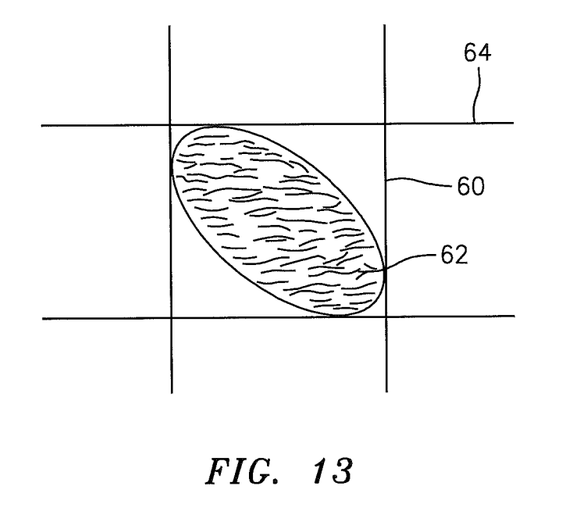
FIG. 13 is a diagrammatic view of a platelet candidate within a bounding box of an orthogonal grid.

The rule based classifier is also adapted to consider a quantitative value representative of the Extent of a platelet candidate. In this feature, a quantitative value representative of the proportion of the pixels in a bounding box 60 that are also within the "segmented mask" 62 is determined, which value is referred to as the Extent. The "segmented mask" 62 refers to the area occupied by the platelet candidate within the bounding box 60. An example of a bounding box 60 is the smallest box in an orthogonal grid 64 that encloses the segmented mask 62. FIG. 13 diagrammatically illustrates a segmented mask 62 of an elliptical-shaped platelet candidate disposed within a bounding box 60 portion of an orthogonal grid 64.

Figure 14:
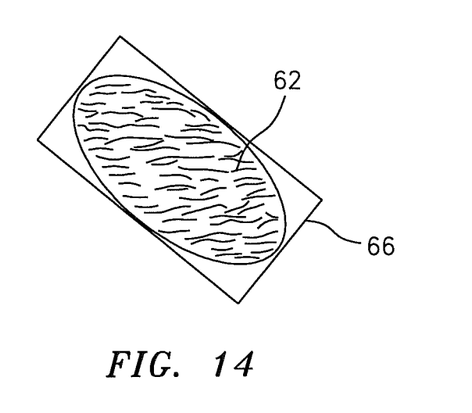
FIG. 14 is a diagrammatic view of the platelet candidate shown in FIG. 14, now disposed within a convex hull.

The rule based classifier is also adapted to consider a quantitative value representative of the Solidity of a platelet candidate. In this feature, a quantitative value representative of the proportion of pixels in the convex hull 66 that are also in the segmented mask 62 is determined, which value is referred to as the Solidity. As indicated above, the segmented mask 62 refers to the area occupied by the platelet candidate. The convex hull 66 can be defined as, for example, the smallest box into which the segmented mask 62 can fit, which hull 66 may not be orthogonally aligned. FIG. 14 diagrammatically illustrates the elliptical-shaped segmented mask 62 shown in FIG. 13, now disposed within a convex hull 66.

The rule based classifier is also adapted to consider a quantitative value representative of the Eccentricity of a platelet candidate. In this feature, a quantitative value representative of a ratio of a distance between the foci of the ellipse and its major axis length is determined.

The rule based classifier is also adapted to consider a quantitative value representative of the Major Axis Length of a platelet candidate. In this feature, a quantitative value representative of the length (in pixels) of the major axis of the ellipse that has the same normalized second central moments as the segmented mask is determined.

The rule based classifier is also adapted to consider a quantitative value representative of the Minor Axis Length of a platelet candidate. In this feature, a quantitative value representative of the length (in pixels) of the minor axis of the ellipse that has the same normalized second central moments as the segmented mask is determined.

The quantitative value of each feature may vary, to some degree, within a sample population from a particular subject, and may also vary between subjects. The present invention addresses this variability by typically utilizing a plurality of features to evaluate a platelet candidate. By using more than one feature to evaluate and identify a platelet candidate, the present method decreases the potential for any particular feature to have an adverse effect on the accuracy of the evaluation. The variability can also be addressed by selectively adjusting the magnitude of the quantitative reference value(s) associated with each feature.

In some embodiments, the rule based classifier is a learned model based classifier. Training sample images are used to train the classifier, and the trained classifier in turn builds the learned model. Once the learned model is developed, that model is then utilized to evaluate features (e.g., such as those described above) associated with a platelet candidate image from a sample, and to include or exclude the platelet candidate based on those features.

The training sample images can be empirically collected platelet images; e.g., platelet images collected by a skilled technician. In some embodiments, the training sample images may be organized in sets associated with each feature. The number of platelet images is selected to provide sufficient data for each feature for training purposes; i.e., sufficient data to enable the classifier to be trained with an acceptable level of accuracy for the feature analysis. The learned model used within this embodiment is not limited to any particular size training set. Often a training set can contain hundreds to thousands of each type of platelet feature to faithfully represent the variability within different people, different imaging conditions and etc.

The classifier can be trained (and the learned model developed) by evaluating each platelet image within a training set to provide quantitative reference value(s) for each feature for each platelet. The collective reference values (or statistical representations thereof) can then be used to build the learned model. The learned models permit the present application to adjust based on actual image data, and the automated interpretation of that image data, and thereby provide a desirable level of accuracy. The present invention is not limited to any particular type of learned model. Examples of acceptable types of learned models include a neural network model such as a Multilayer Perceptron, or a statistical model such as a Bayesian classifier, or a linear model such as a Support Vector Machine (SVM). All these types of learned models are well known and the present invention is not limited to any particular embodiment thereof. In some embodiments, combinations of these models (and/or others) can be used.

In the operation of the invention, an undiluted sample of whole blood is collected into a disposable cartridge such as that illustrated in FIGS. 2-5. Reagents, including one or more colorants (e.g., ACO) and an anticoagulant (e.g., EDTA), are added to the sample to facilitate the platelet analysis. The sample admixed with the reagents is deposited within the analysis chamber portion of the cartridge, where it quiescently resides during the imaging process. The cartridge is inserted into (or otherwise engaged with) the analysis device 22, where it is appropriately positioned by the cartridge positioner 36 relative to the objective lens, sample illuminator 38, and image dissector 40, and is subsequently imaged.

In most instances, the analysis device 22 is programmed to image the entirety of the sample quiescently residing within the chamber 24. In some applications, however, a portion of the sample can be imaged. The imaging process can vary depending upon the application at hand. For the platelet analysis described above, the imaging process involves subjecting the sample to a fluorescent excitation light source; e.g., light at about 470 nm from the epi-fluorescent light source. The excitation light source causes the colorant combined with elements disposed within the sample to emit fluorescent light at two different wavelengths (e.g., red ~660 nm, and green ~540 nm). The image dissector 40 captures the light fluorescing from the sample and provides signals representative of the intensity and color (i.e., wavelength) of the captured light. The signals are processed into a form that permits the programmable analyzer 42 to form an image of the sample based on the signals, which image can be quantitatively analyzed to perform the platelet analysis.

Figure 15:
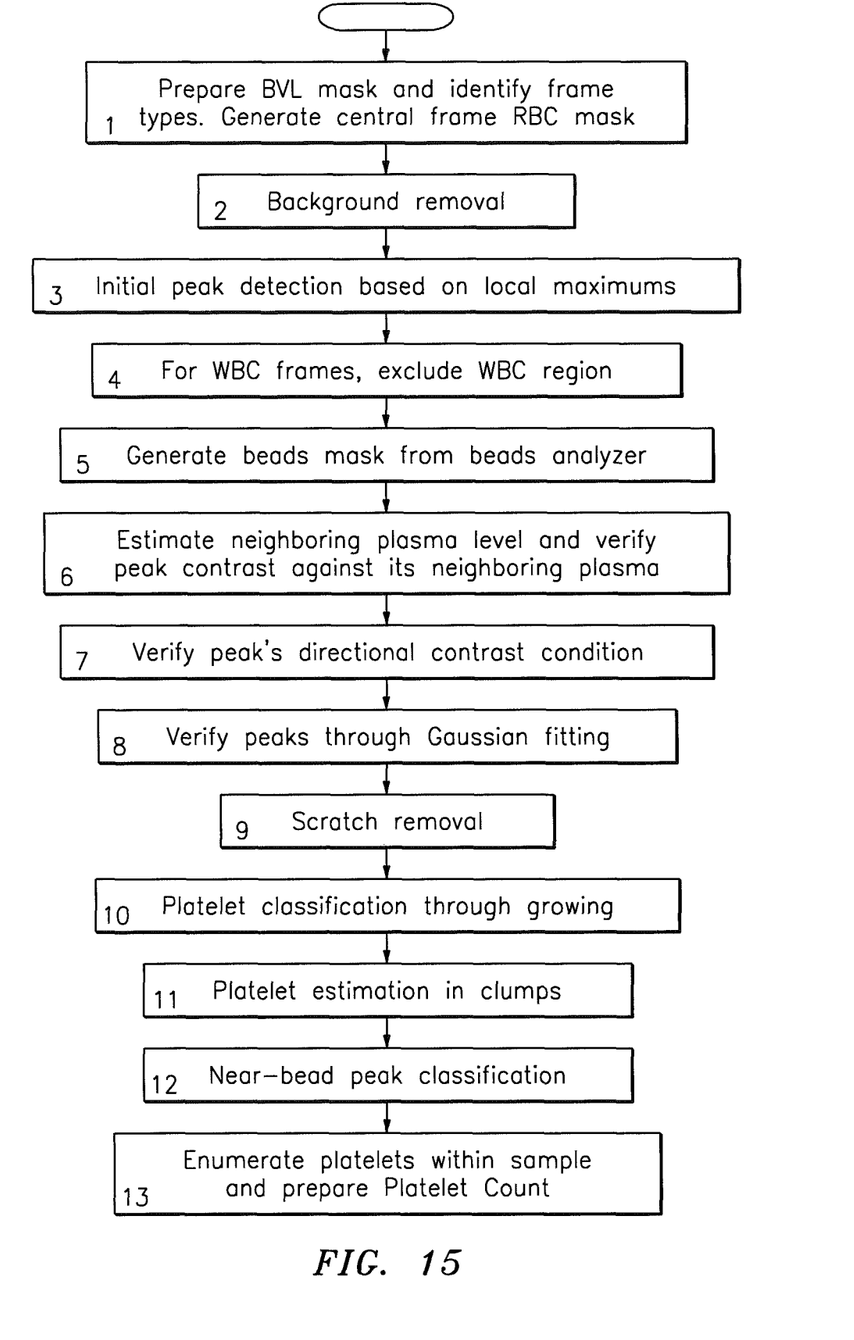
FIG. 15 is a flow chart illustrating an embodiment of the present method for identifying platelets within a sample via images of the sample.

The flow chart shown in FIG. 15 provides an example of the process through which the platelets 52 in a sample, imaged as described above, can then be identified and enumerated according to the present invention. The present invention does not require all of the steps identified in FIG. 15 be performed in all embodiments, and also is not limited to the particular order of steps shown in FIG. 15.

The first step shown in FIG. 15 involves applying a blood volume mask to the image to determine the area occupied by the sample within the image, which can then be used to determine the volume of the sample within the analysis chamber 24. A RBC mask can also be generated for later use in distinguishing platelets 52 in certain regions.

The second step involves removal of background from the sample image. As indicated above, background portions of the images can be identified by various techniques including thresholding, and once identified can be removed by filter, segmentation, etc.

The third step involves identifying image intensity peaks by identifying local intensity maximums in a given area of image.

The fourth step involves identifying WBCs 50 within the sample image, or image portions, and excluding those regions as image intensity regions that are not platelet candidates.

The fifth step involves identifying beads 31 within the sample image and preparing a mask that can be applied to the image portions representing beads 31.

The sixth step involves estimating plasma intensity in local regions where required to identify platelets 52; e.g., local plasma intensity values can be used to distinguish local intensity peaks attributable to platelets 52 from local intensity peaks attributable to plasma. This step may be performed selectively in particular regions within the sample; e.g., regions containing large numbers of RBCs 54.

The seventh step involves analyzing particular platelet candidates to determine whether the image intensity peak of the candidate has directional contrast in one or more directions extending outwardly from the peak.

The eighth step involves analyzing the Gaussian distribution of the image intensity of particular platelet candidates. The nature of the distribution, as described above, provides information relating to the probability of a particular candidate being an actual platelet.

The ninth step involves removal of elements within the sample image that are attributable to imperfections present in the imaging system; e.g., scratches in the analysis chamber panels, debris on the panels, etc.

The tenth step involves identifying platelets 52 from candidates using an image growing technique. This technique can be applied to a variety of different types of platelet candidates. For example, the growing technique can be applied to a platelet candidate that is identified as a potential platelet clump. The growing technique, an example of which is described above, provides a means to evaluate the area occupied by the platelet candidate (or clump). The area provides information that can be used subsequently to evaluate whether the candidate is actually a platelet. If the candidate is a clump, the area provides information that can be used to determine the number of platelets 52 residing within the clump.

The eleventh step involves estimating the number of platelets 52 within those candidates determined to be clumps. Examples of mathematical techniques that can be used to estimate the number of platelets 52 within a clump are described above. The present invention is not limited to these particular algorithms.

The twelfth step involves classifying platelet candidates that are located in close proximity to separator beads 31 disposed within the chamber 24. As indicated above, in some embodiments of the present invention the programmable analyzer 42 is adapted with an algorithm that includes a rule based classifier that may include a learned model. The platelet candidates are evaluated using the classifier and the identified platelets 52 are enumerated.

Once the actual platelets 52 are identified, the platelets 52 within the determined sample volume can be reported in a platelet number per volume value, or other useful form, as indicate in the thirteenth step.

Although this invention has been shown and described with respect to the detailed embodiments thereof, it will be understood by those skilled in the art that various changes in form and detail thereof may be made without departing from the spirit and the scope of the invention.

What is claimed is:

1. A method for identifying platelets within a whole blood sample, comprising:
adding at least one colorant to the whole blood sample, which colorant is operable to tag platelets;
disposing the blood sample into a chamber defined by at least one transparent panel;
imaging at least a portion of the sample quiescently residing within the chamber to create at least one image comprised of incremental units, each unit having an intensity value; and
identifying one or more platelet candidates within the image based on per unit intensity value differences in local regions within the image;
identifying at least one platelet from the identified platelet candidates using an analyzer adapted to identify the platelet based on quantitatively determinable features associated with the per unit intensity values, and based on a directional contrast of per unit intensity values extending outwardly from a peak intensity.

2. The method of claim 1, wherein the step of identifying one or more platelet candidates includes applying a global threshold to the intensity value differences within the image and eliminating those platelet candidates having an intensity value difference below the threshold.

3. The method of claim 1, further comprising identifying anomaly image portions and estimating the number of platelets in the anomaly image portions.

4. The method of claim 1, wherein the step of identifying one or more platelet candidates includes accounting for an image intensity of plasma.

5. The method of claim 1, further comprising determining a value of an incremental decrease in per unit intensity value within the image in a direction extending away from the peak intensity.

6. The method of claim 5, further comprising determining a circumferential uniformity of the incremental decrease in per unit intensity value.

7. The method of claim 5, further comprising determining a Gaussian distribution of the incremental decrease in per unit intensity value.

8. The method of claim 1, wherein the step of identifying one or more platelet candidates includes evaluating the image to determine a presence of one or more platelet clusters within the sample.

9. The method of claim 1, wherein the step of identifying at least one platelet from the identified platelet candidates includes analyzing one or more of the platelet candidates using a rule based classifier.

10. The method of claim 1, wherein the intensity values are representative of emitted fluorescent light intensity.

11. An apparatus for identifying platelets within a whole blood sample, comprising:
an analysis cartridge having an analysis chamber with a pair of planar members, at least one of which is transparent, which cartridge is operable to add at least one colorant to the whole blood sample, which colorant is operable to tag platelets, and which chamber is operable to hold the sample quiescently between the planar members; and
an analysis device that is operable to image at least a portion of the sample quiescently residing within the chamber to create at least one image comprised of incremental units, each unit having an intensity value, and operable to identify one or more platelet candidates within the image based on per unit intensity value differences in local regions within the image, and operable to identify at least one platelet from the identified platelet candidates based on quantitatively determinable features associated with the per unit intensity values, and based on a directional contrast of per unit intensity values extending outwardly from a peak intensity.

12. The apparatus of claim 11, wherein the analysis device is adapted to apply a global threshold to the intensity value differences within the image and eliminating those platelet candidates having an intensity value difference below the threshold.

13. The apparatus of claim 11, wherein the analysis device is adapted to identify anomaly image portions and estimate the number of platelets in the anomaly image portions.

14. The apparatus of claim 11, wherein the analysis device is adapted to account for an image intensity of plasma.

15. The apparatus of claim 11, wherein the analysis device is adapted to determine a value of an incremental decrease in per unit intensity value within the image in a direction extending away from the peak intensity.

16. The apparatus of claim 15, wherein the analysis device is adapted to determine a circumferential uniformity of the incremental decrease in per unit intensity value.

17. The apparatus of claim 15, wherein the analysis device is adapted to determine a Gaussian distribution of the incremental decrease in per unit intensity value.

18. The apparatus of claim 11, wherein the analysis device is adapted to evaluate the image to determine a presence of one or more platelet clusters within the sample.

19. The apparatus of claim 11, wherein the analysis device is adapted to analyze one or more of the platelet candidates using a rule based classifier.

20. The apparatus of claim 11, wherein the intensity values are representative of emitted fluorescent light intensity.

* * * * *